United States Patent [19]

Cox

[11] Patent Number: 4,475,547

[45] Date of Patent: Oct. 9, 1984

[54] ANIMAL EAR SUPPORT DEVICE

[76] Inventor: James O. Cox, P.O. Box 107, Carthage, Miss. 39051

[21] Appl. No.: 448,513

[22] Filed: Dec. 10, 1982

[51] Int. Cl.³ .............................................. A01K 29/00
[52] U.S. Cl. ..................................... 128/133; 119/96
[58] Field of Search ................ 128/133, 80 A; 119/96

[56] References Cited

U.S. PATENT DOCUMENTS

| 2,587,966 | 10/1950 | Cleary | 128/346 |
|---|---|---|---|
| 3,257,990 | 6/1966 | Robertson et al. | 119/96 |
| 3,970,080 | 7/1976 | White | 119/96 |
| 4,059,106 | 11/1977 | Shannon | 128/133 |
| 4,148,279 | 4/1979 | Hoytt | 128/133 |
| 4,221,189 | 9/1980 | Olvera | 128/133 |
| 4,250,875 | 2/1981 | Marsh et al. | 128/133 |
| 4,327,714 | 5/1982 | Spann | 128/80 A |

Primary Examiner—Kyle L. Howell
Assistant Examiner—John C. Hanley
Attorney, Agent, or Firm—Scrivener, Clarke, Scrivener & Johnson

[57] ABSTRACT

A brace is provided for positioning on the top of a dog's head after ear cropping surgery and has side walls having the shape of the cropped ears to which the cropped ears are connected until healed. The brace may be provided with stationary nylon self-gripping tape on each side wall or an adhesive such as cattle glue may be used to attach the ears to the side walls of the brace.

5 Claims, 6 Drawing Figures

ANIMAL EAR SUPPORT DEVICE

SUMMARY OF THE INVENTION

A solid body is provided which is constructed and adapted to be positioned on the head of a dog after ear crop surgery to hold the cropped ears in an upright position. The device is made of a lightweight material, preferably styrofoam, and has a base shaped to fit the usual shape of the top of the dog's head and flat upwardly converging side surfaces which have the shape of the cropped ear. The side surfaces may be covered with a nylon self-gripping tape or may be left uncovered for attachment of the ears with an adhesive such as cattle glue.

DESCRIPTION OF THE INVENTION

Figure 1:
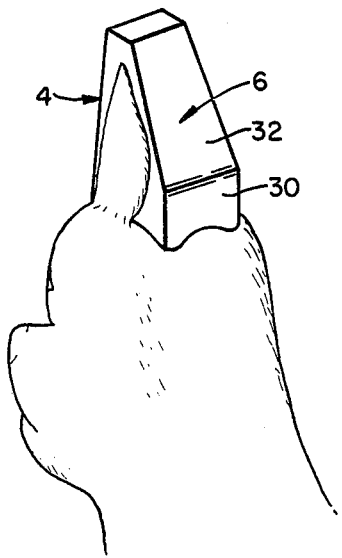
FIG. 1 is a perspective view of the head of a dog showing the brace provided by the invention with the ears attached.

It is often desirable for aesthetic and other reasons of style to crop the ears of certain breeds of dogs and to train the ears to stand erect. This procedure is performed, for example, on large dogs such as Great Danes, medium sized dogs such as Boxers and Dobermans, and small dogs such as Schnauzers. By this invention I have provided a brace which fits on top of the dog's head and to which the cropped ears may be releasably attached and left so attached until they have permanently assumed their intended erect condition.

The preferred form of the brace provided by the invention is illustrated in the drawings forming a part of this specification, and comprises a solid body formed of a lightweight synthetic material, preferably styrofoam, the configuration and dimensions of which permit it to be positioned on the top of a dog's head between the ears and the ears attached to its side wall surfaces, and which may be made in various sizes to fit dogs of all size classifications.

Figure 2:
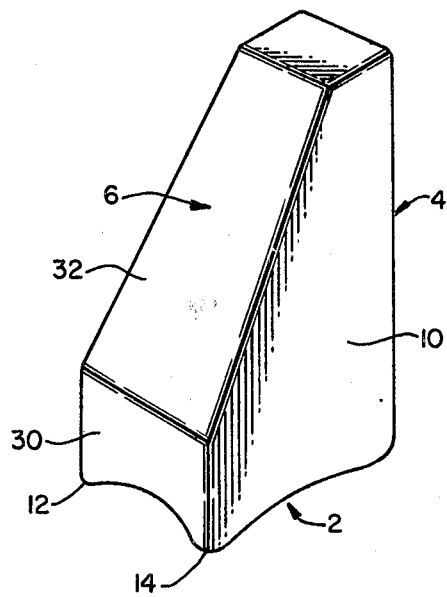
FIGS. 2, 3, 4 and 5 are, respectively perspective, side, rear and front views of the brace.
Figure 3:
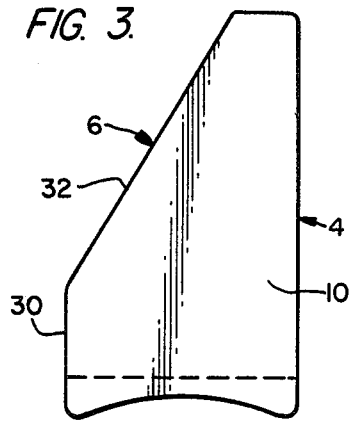
Figure 5:
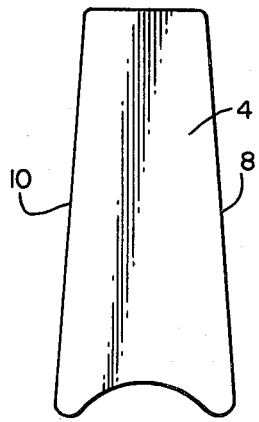

The brace has a base 2, a front wall 4, a rear wall 6, and side walls 8, 10 which converge from the base upwardly. The base has downwardly convex ridges 12, 14 extending from front to rear and forming the lower edges of the side walls, and each of these edges and the base itself are upwardly curved on an arc from front to rear, as shown in FIGS. 2 and 3. This configuration of the base permits the brace to be comfortably and firmly positioned on the top of the dog's head, the width of the brace being such that the lower edges 12, 14 of its sides are positioned adjacent the junctures of the ears with the top of the head, as shown in FIG. 1.

The side walls 8, 10 of the brace are flat and identical in shape and are shaped to conform to the cropped shape of the ears, and each side wall therefore has a rear edge which comprises a lower vertical part 20 of relatively small height which is surmounted by an upper part 22 of relatively great height which is inclined in the direction of the front wall 4.

The rear wall 6 has a lower segment 30 which connects the lower edges 20 of the side walls, and an upper segment 32 which connects the upper edges 22 of the side walls, and is therefore inclined toward the front wall 4. The front wall 4 connects the front edges of the side walls and is therefore vertical itself and is flat.

Figure 6:
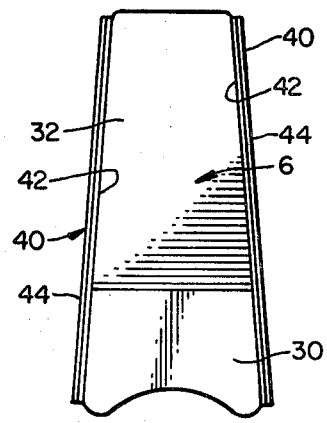
FIG. 6 is a rear view of the brace showing the embodiment in which nylon self-gripping tape is attached to both side wall surfaces.
Figure 4:
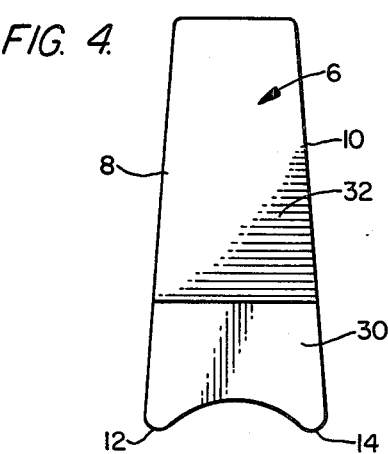

In an preferred embodiment of the invention which is illustrated in FIG. 6 a self-gripping tape 40 is attached to each side wall and the brace is made and sold in this configuration. This tape comprises a normally central layer 42 which is adhesive on both surfaces, and normally has a non-adhesive layer covering each adhesive surface, one of which is removed to cause the remainder of the tape to be connected to and form part of the brace, the adhesive layer 42 being covered by the non-adhesive layer 44 until the brace is used.

If the embodiment of FIG. 6 is not used the side wall surfaces of the brace are left uncovered ready for adhesive attachement of the ears, as will be described.

ATTACHMENT OF THE EARS TO THE BRACE

1. Place the brace squarely on the top of the dog's head and settle it comfortably between the ears.

2. Attach outside of taped ear to adhesive backed nylon self-gripping tape. Set brace on top of head directly between the ears. Pull each ear up and stick to sides of brace. Apply slight tension to tips of ears as they are pulled up toward the apex of brace and fasten the self-gripping tape; or 3. When using the brace having sides without the stationary self-gripping tape spread each side of the brace with an adhesive such as cattle glue and finger tip pressure hold taped ears against glued sides for 1 to 2 minutes to fix.

I claim:

1. A brace for supporting the ears of a dog in erect position after ear crop surgery, comprising:
    (a) a solid body having a base, side surfaces, and front and rear surfaces, and having the following configuration:
        i. the base being transversely concave forming a passage from front to rear adapted to fit the crowned head of a dog,
        ii. the side surfaces being flat and upwardly convergent at a slight angle from the base, and each having a lower edge which is upwardly curved from the front surface to the rear surface,
        iii. the front surface being flat and extending upwardly from the base at substantially a right angle,
        iv. the rear surface comprising a relatively short flat lower part extending upwardly from the base at substantially a right angle, and a relatively long flat upper part extending angularly upwardly from the upper end of the lower part toward the front surface, and
    (b) adhesive means on each side surface for attaching the ears of a dog to the solid body.

2. An ear brace according to claim 1, which is made of a lightweight material.

3. An ear brace according to claim 1 which is made of lightweight styrofoam.

4. An ear brace according to claim 1, in which the vertical height of the side walls above the base is greater than the front-to-rear and side-to-side dimensions of the base.

5. An ear brace according to claim 1, wherein said adhesive means comprises a nylon layer adhesively attached to the side surface and having an outer adhesive surface covered by a non-adhesive removable layer.

* * * * *